United States Patent [19]

Rochling et al.

[11] 3,966,932

[45] June 29, 1976

[54] TRIAZINO-BEZIMIDAZOLE FUNGICIDES

[75] Inventors: Hans Röchling, Altenhain, Taunus;
Kurt Härtel, Hofheim, Taunus, both of Germany

[73] Assignee: Hoechst Aktiengesellschaft, Frankfurt am Main, Germany

[22] Filed: Dec. 26, 1974

[21] Appl. No.: 536,399

Related U.S. Application Data

[62] Division of Ser. No. 361,073, May 14, 1973, Pat. No. 3,896,120.

[30] Foreign Application Priority Data

May 18, 1972 Germany............................ 2224244
Feb. 19, 1973 Germany............................ 2308067

[52] U.S. Cl.................................. 424/249; 424/248
[51] Int. Cl.²............................................ A01N 9/22
[58] Field of Search............................ 424/248, 249; 260/249.5

[56] References Cited

UNITED STATES PATENTS

| | | | |
|---|---|---|---|
| 2,444,609 | 7/1948 | Heimbach et al............. | 260/249.5 X |
| 3,309,366 | 3/1967 | Schlapfer et al.............. | 260/249.6 |
| 3,896,120 | 7/1975 | Röchling et al............... | 260/249.5 |

*Primary Examiner*—Leonard Schenkman
*Attorney, Agent, or Firm*—Curtis, Morris & Safford

[57] ABSTRACT

Triazino-benzimidazoles of the formula

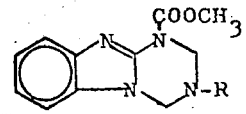

in which R is a variety of substituents including alkyl, cycloalkyl, bi- and tricycloalkyl, phenyl and phenalkyl, are valuable fungicides.

6 Claims, No Drawings

TRIAZINO-BEZIMIDAZOLE FUNGICIDES

This is a division of application Ser. No. 361,073, filed May 14, 1973 and now U.S. Pat. No. 3,896,120.

The present invention relates to triazino-benzimidazoles of the formula I

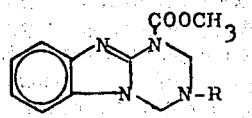

where
R is alkyl having from 1 to 18 carbon atoms; alkenyl having from 3 to 18 carbon atoms, alkinyl having from 2 to 8 carbon atoms, cycloalkyl having from 3 to 12 carbon atoms, optionally substituted by one or more alkyl groups having from 1 to 4 carbon atoms or by hydroxy;
cyclohexylalkyl, cyclohexylalkenyl, or cyclohexylalkinyl each having from 1 to 3 carbon atoms in the chain, endomethylene-cyclohexylmethyl, endomethylene-cyclohexenylmethyl, tricyclodecyl, or tricyclodecenyl; phenalkyl, diphenylalkyl or triphenylalkyl each having from 1 to 6 carbon atoms in the alkylene radical, the phenyl nuclei of which being optionally substituted by halogen, alkyl, alkoxy, alkylthio each having from 1 to 4 carbon atoms or di-($C_1$-$C_4$)-alkyl amino;
phenyl or naphthyl, optionally being substituted each by alkyl having from 1 to 4 carbon atoms, halogen, halogeno-alkyl having from 1 to 4 carbon atoms, trifluoromethyl, hydroxy, alkoxy having from 1 to 4 carbon atoms, phenoxy of ($C_1$-$C_4$)-alkylthio; di-($C_1$-$C_4$)-alkyl-amino-($C_2$-$C_6$)-alkyl; hydroxy-($C_2$-$C_{12}$)-alkyl, ($C_2$-$C_{18}$)-alkoxyalkyl or dialkoxyalkyl, ($C_2$-$C_{18}$)-alkylmercaptoalkyl, ($C_3$-$C_9$)-dialkylphosphinyl-alkyl, furfuryl-alkyl, morpholino-($C_1$-$C_4$)-alkyl pyrrolidino-($C_1$-$C_4$)-alkyl, piperidino-($C_1$-$C_4$)-alkyl or ($C_2$-$C_{12}$)-carbalkoxylalkyl.

The present invention relates furthermore to a process for the preparation of compounds of formula I, which comprises reacting 2-methoxycarbonylamino-benzimidazole of the formula II

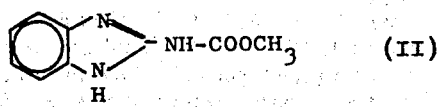

with a primary amine of the formula $H_2NR$ (III) and formaldehyde.

A preferred embodiment of the precess of the present invention is the following: The 2-methoxycarbonylamino-benzimidazole (II) is suspended or dissolved in a solvent, the molar to twice molar amount of the amine is added and subsequently, with agitation, the two to four times molar amount of an aqueous formaldehyde solution is added. The operational temperature is advantageously kept at 0° to 80°C, especially 20° to 40°C, but the temperature range is not critical. The reaction product normally dissolves and may be separated by filtering the solution from a 2-methoxycarbonylamine-benzimidazole residue; concentration of the solution and treatment with an inert solvent, such as gasoline, or reprecipitation, for example from methylene chloride/gasoline, yields the triazinobenzimidazole in pure form.

The reaction always proceeds with formation of the final product I, even when there is a deficiency of formaldehyde.

Preferred amines of formula III for the reaction are those in which R is straight-chain or branched alkyl having from 1 to 15 carbon atoms; alkenyl having from 3 to 18 carbon atoms; cycloalkyl having from 3 to 12 carbon atoms, which may be substituted by alkyl having from 1 to 4 carbon atoms, especially by methyl or ethyl; tricyclodecyl, phenyl or naphthyl; phenyl or naphthyl mono- or di-substituted by methyl, ethyl, tert.-butyl, chlorine or hydroxy; phenylalkyl having from 7 to 9 carbon atoms, especially benzyl, or diphenylalkyl having from 13 to 14 carbon atoms the phenyl groups of which may be substituted by chlorine or methyl; alkoxy-alkyl, dialkoxyalkyl or alkylmercaptoalkyl having from 3 to 8, especially from 3 to 4 carbon atoms; hydroxyalkyl having from 3 to 7, especially from 3 to 6 carbon atoms; dialkyl-phosphinylalkyl having from 3 to 9, especially from 3 to 5 carbon atoms; morpholino-alkyl having from 5 to 8, especially from 6 to 7 carbon atoms, or carbalkoxy having from 3 to 12, especially from 4 to 8 carbon atoms.

Besides the amines used in the examples, the following amines may therefore be used: iso-amylamine, iso-octylamine, nonylamine, n-decylamine, iso-decylamine, n-undecylamine, pentadecylamine, hexadecylamine, octadecylamine, n-octadecen-9-ylamine, cyclobutylamine, 2-methylcyclopentylamine, N,N-dimethyl-, N,N-diethyl, N,N-dibutyl, N,N-methylethyl-, N-methyl-N-propyl-, N-ethyl-N-isobutylethylene-diamine or the corresponding propylenediamines, tetramethylene-diamines and hexamethylene-diamines, 3-aminohexahydro-toluene, 4-amino-hexahydro-m-xylene, 4-isopropylcyclohexylamine, 4-ethyl-cyclohexylamine, 2,6-diethylaniline, 4-tert.-butylamiline, 2-, 3- and 4-chloroaniline, 2-, 3- and 4-aminophenol, α- and β-naphthylamine, 3-phenylpropylamine, 2-phenylethylamine, 4-phenyl-butylamine, diphenylmethylamine, 2,2-diphenylethylamine, 2-, 3- and 4-chlorobenzylamine, 2-(2'-chlorophenyl)-ethylamine, 2-, 3- and 4-methylbenzylamine, 2-ethylthio-ethylamine, 4-methylthio-butylamine, 1- and 4- amino-hexanol, dimethyl-(2-amino-ethyl)-phosphine oxide, diethyl(4-aminobutyl)-phosphine oxide, N-aminomethyl-morpholine, N-(3-aminopropyl)-morpholine, N-aminoethyl-pyrrolidine, N-aminomethyl- and N-aminoethyl-piperidine, furfurylamine, aminoacetic acid methyl- and -ethyl ester, 2-aminoproprionic acid methyl ester, 3-aminobutyric acid ethyl ester, 6-aminocapronic acid methyl- and -ethyl ester, alanine methyl ester, γ-aminovaleric acid methyl- and -ethyl ester, 4-methoxybenzylamine, 4-tert.-butyl-cyclohexylamine, 2-amino-1,3,5-trimethylbenzene, 2-aminobutane, 2-ethylhexylamine, n-tridecylamine and tetradecylamine, or iso-tetradecylamine.

Suitable solvents for the reaction are above all moderately or weakly polar solvents, preferably those having a low boiling point, for example methylene chloride, chloroform, carbon tetrachloride, benzene; ethers such as diethyl ether, di-isopropyl ether or tetrahydrofuran; esters such as methyl acetate or ethyl acetate; or ketones such as acetone or methylethyl ketone. Preferably, chloroform or methylene chloride are used.

The 2-methoxycarbonylamine-benzimidazole may be prepared according to the method described in J. Am.

Chem. Soc. 56, 144 (1934), by reaction of O-phenylene-diamine with S-methyl-isothiourea dicarboxylic acid dimethyl ester. The preparation of the amines required for the reaction is also known from the literature.

The compounds of the invention have an excellent fungicidal, especially systemic, action, so that they can be used for combating fungus germs having already intruded into the plant tissue in a curative manner. This is especially important in the case of those fungus diseases which have a long incubation period and, after the outbreak of the infection, cannot be combated any more by the usual fungicides. The activity range of these compounds is very broad and includes a series of fungus germs important in crop farming, fruit growing, viticulture, hop growing, or horticulture, as for example Fusicladium Spp, Gloeosporium Spp, Cylindrosporium Spp, Botrytis Spp, Verticillium Spp, Cercospora Spp, Septoria Spp, Mycosphaerella Spp, Cladosporium Spp, Colletotrichum Spp, Rhizoctonia Spp, Fusarium Spp, Cercosporella Spp, ustilagineae, erysiphaceae, aspergillaceae or sclerotinaceae.

Furthermore, a number of the compounds of the invention, especially those having long-chain radicals, have an excellent activity against phycomycetes, such as the Peronospora or Phytophthora species. Their degree of efficiency in this particular respect is equal to that of the metal salts of dithiocarbamic acid or the N-trichloromethylthio-phthalimide derivatives, and in many cases is even superior to them.

The compounds of the invention may also be used for protecting stored fruits or vegetables against fungus infection (for example species of Fusarium or Penicillium and the like.)

Furthermore, they are suitable for technological application, for example for protecting textiles, wood, dyes or coatings against infection with rot and other fungus germs.

The present invention therefore relates to pesticides, especially fungicides, containing the triazino-benzimidazoles of formula I as active substance, especially in concentrations of from 2 to 95 %, in combination with usual formulation additives such as solid or liquid inert carriers, adhesives, wetting and dispersing agents and/or grinding auxiliaries in the form of wettable powders, emulsions, suspensions, dusting powders or granules. They may be mixed with other fungicides with which they form compatible mixtures.

As carrier material, mineral substances, for example aluminium silicates, argillaceous earths, kaolin, chalks, siliceous chalks, talcum, kieselguhr or hydrated silicic acids can be used, or preparations of these mineral substances with special additives, for example chalk with sodium stearate. As carrier material for liquid preparations, all usual and suitable organic solvents may be employed, for example toluene, xylene, diacetone alcohol, isophorone, gasolines, paraffin oils, dioxan, dimethyl formamide, dimethyl sulfoxide, ethyl acetate, tetrahydrofuran, chlorobenzene, and the like.

Suitable adhesives are glue-like cellulose products or polyvinyl alcohols.

As wetting agents, all suitable emulsifiers may be used, for example ethoxylated alkylphenols, salts of aryl- or alkyl- aryl-sulfonic acids, salts of oleyl-methyl-taurine or of ethoxylated benzenesulfonic acids, or soaps.

Suitable dispersing agents are cellulose pitch (salts of ligninsulfonic acid, salts of naphthalenesulfonic acid or salts of oleyl-methyl-taurine.

As grinding auxiliaries, suitable inorganic or organic salts, for example sodium sulfate, ammonium sulfate, sodium carbonate and sodium bicarbonate, sodium thiosulfate, sodium stearate, or sodium acetate may be used.

Furthermore, the compounds of formula I have an anthelmintic activity in the veterinary field and may therefore be used for combating different worm diseases in domestic animals and productive livestock The following examples of preparation and application illustrate the invention.

EXAMPLES OF PREPARATION

EXAMPLE 1

57.3 g (0.3 mole) of 2-methoxycarbonylamino-benzimidazole were suspended in 550 ml of methylene chloride, 55.5 g (0.3 mole) of dodecylamine were added and the whole was heated to 35°C. At this temperature, 68 ml (0.8 mole) of aqueous 35 % formaldehyde solution were added dropwise with agitation, which was continued subsequently for 1 hour at 38°C, before the mixture was allowed to cool, also with agitation.

The non-converted 2-methoxycarbonylamino-benzimidazole was suction-filtered, the aqueous layer was separated and the methylene chloride solution was dryed over magnesium sulfate and concentrated, yielding 122.7 g of a crystalline substance having a melting point of 75°C.

In order to eliminate adhering amine, this substance was stirred with 200 ml of gasoline (30/85°C); thus obtaining 95 g (79 % of the theoretical yield) of 1-methoxycarbonyl-3-dodecyl-s-hexahydrotriazino-benzimidazole having a melting point of 86° to 87°C.

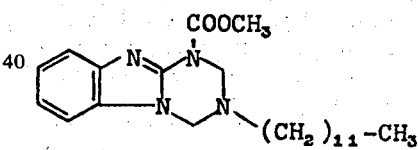

$C_{23}H_{36}N_4O_2$ molecular weight: 400 calc: C 69.0 %; H 9.0 %; N 14.0 %
found: C 69.3 %; H 9.2 %; N 14.0 %

In the infrared spectrum, the compound had a characteristic carbonyl absorption at 1720 cm$^{-1}$, as well as double bond bands at 1620 cm$^{-1}$ and 1595 cm$^{-1}$.

EXAMPLE 1 a 57.3 g (0.3 mole) of 2-methoxycarbonylamino-benzimidazole were suspended in 900 ml of methylene chloride, and 39 g (0.3 mole) of 3-diethylamino-1-propylamine were added. The suspension was heated to 35°C. At this temperature, 60 ml (0.7 mole) of 35 % formaldehyde solution were added dropwise with agitation, which was then continued at 38°C for 2 hours, before the mixture was allowed to cool, also with agitation.

The non-converted 2-methoxycarbonylamino-benzimidazole was suction-filtered, the aqueous layer was separated, and the methylene chloride solution was dried over magnesium sulfate and concentrated, yielding an oily residue which was stirred at 30° to 85°C with gasoline. After decanting, the gasoline solution was concentrated, the oily residue obtained was redissolved in methylene chloride and washed twice with water. The methylene chloride solution was then dried over MgSO₄, concentrated, and the oily residue was degassed at room temperature under highly reduced pressure. Yield: 37 g (36 % of the theoretical yield) of a non-distillable oil.

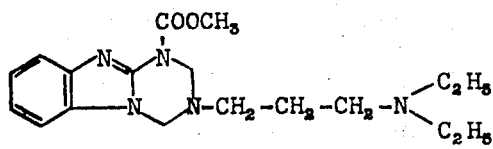

$C_{18}H^{"}N_3O_2$ MW: 345
calc. : C 62.6 %; H 7.8 %; N 20.2 %
found: C 63.0 %; H 8.5 %; N 19.8 %

EXAMPLE 2

38.2 g (0.2 mole) of 2-methoxycarbonylamino-benzimidazole were suspended in 600 ml of chloroform, 14.6 g (0.2 mole) of n-butylamine were added, and the whole was heated to 35°C. At this temperature, 68 ml (0.8 mole) of 35 % aqueous formaldehyde solution was added dropwise, with agitation, which was then continued at 38°C for 1 hour. The benzimidazole dissolved while reacting. The mixture was allowed to cool, the aqueous layer was eliminated, and the organic phase was dried over magnesium sulfate.

After filtration and concentration, an oil was obtained which solidified after trituration with n-hexane. Yield: 41 g (71 % of the theoretical yield) of 1-methoxy-3-nbutyl-s-hexahydro-triazino-benzimidazole; melting point 109°C.

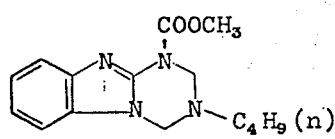

$C_{15}H_{20}N_4O_2$   MW 288 calc. : C 62.5 %; H 6.94 %; N 19.45 %
found : C 62.8 %; H 7.2 %; N 19.5 %

In the infrared spectrum, the compound showed a carbonyl absorption at 1745 cm⁻¹, and double bond bands at 1620 cm⁻¹.

EXAMPLE 3

57.3 g (0.3 mole) of 2-methoxycarbonylamino-benzimidazole were suspended in 900 ml of methylene chloride, 26.7 g (0.3 mole) of 3-methoxy-propylamine were added and the whole was heated to 35°C. At this temperature, 68 ml (0.8 mole) of aqueous 35 % formaldehyde solution were added dropwise, with agitation, which was subsequently continued at 38°C for 1 hour.

After cooling, the mixture was filtered off a small amount of non-converted starting benzimidazole. The aqueous phase was separated, and the methylene chloride solution was dried over magnesium sulfate.

After filtration and concentration, an oil was obtained which solidifies on trituration with n-hexane. Yield: 63 g (69 % of the theoretical yield) of 1-methoxycarbonyl-3-(3'-methoxypropyl)-s-hexahydro-triazino-benzimidazole. Melting point: 73° to 74°C.

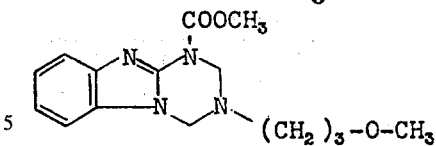

$C_{15}H_{20}N_4O_3$   MW 304 calc. : C 59.2 %; H 6.6 %; N 18.7 %
found: C 59.3 %; H 6.9 %; N 18.7 %

In the infrared spectrum, the compound showed a carbonyl absorption at 1750 cm⁻¹, and double bond bands at 1625 cm⁻¹ and 1600 cm⁻¹. The substances of the formula

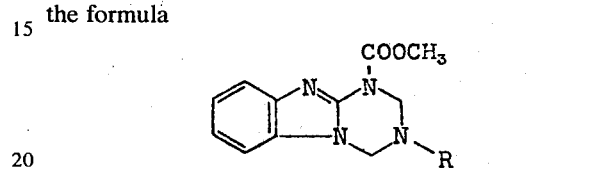

as indicated in the following Table are prepared according to Examples 1 to 3.

Table

| Example | R | Melting point °C |
|---|---|---|
| 4 | —CH₃ | 138 |
| 5 | —C₂H₅ | 167–168 |
| 6 | —C₃H₇ (n) | 130–132 |
| 7 | —C₃H₇ (iso) | 112–114 |
| 8 | —CH—CH=CH₂ | 106–108 |
| 9 | —C(CH₃)₃ | 143 |
| 10 | —CH(CH₃)(CH₂—CH₃) | 136 |
| 11 | —C₄H₉ (iso) | 138 |
| 12 | —C₈H₁₇ (n) | 76–78 |
| 13 | —C₉H₁₉ (iso) | 139 |
| 14 | —C₁₃H₂₇ (iso) | non-distillable oil |
| 15 | —C₆H₁₃ (n) | 75–76 |
| 16 | —(CH₂)₃—OH | 154 |
| 17 | —CH₂—CH(OH)—CH₃ | 110–112 |
| 18 | —CH(CH₂OH)(CH₂—CH₃) | 128–130 |
| 19 | —(CH₂)₅—OH | 86–88 |
| 20 | cyclopentyl | 130–132 |
| 21 | cyclopropyl | 165 |
| 22 | cyclohexyl | 155–156 |
| 23 | cyclooctyl | 171 |
| 24 | —CH₂—phenyl | 145–146 |
| 25 | —(CH₂)₂—S—CH₃ | 107–109 |
| 26 | —(CH₂)₃—S—CH₃ | 120–121 |
| 27 | —(CH₂)₃—O—C₂H₅ | 84–85 |
| 28 | —(CH₂)₃—O—C₃H₇ | 66–67 |
| 29 | —(CH₂)₂—N(morpholino) | 66–68 |
| 30 | —CH₂—CH₂—phenyl(phenyl) | 40–45 |

Table-continued

| Example | R | Melting point °C |
|---|---|---|
| 31 | −CH₂−CH(CH₃)−C₆H₅ | non-distillable oil |
| 32 | −(CH₂)₃−CH(OC₂H₅)₂ | non-distillable oil |
| 33 | −C₇H₁₅ (n) | 73–74 |
| 34 | cycloheptyl | 118–120 |
| 35 | tricyclic (norbornyl-type) | 133–134 |
| 36 | −C(CH₃)₂−CH₂−C(CH₃)₂−CH₃ | 151–152 |
| 37 | −CH[(CH₂)₅CH₂][(CH₂)₅] (cyclic) | 125–126 |
| 38 | −(CH₂)₂−O−CH₃ | 99 |
| 39 | −C₅H₁₁ (n) | 106–107 |
| 40 | −C₉H₁₉ (n) | 100–102 |
| 41 | −(CH₂)₃−O−C₄H₉ | non-distillable oil |
| 42 | −(CH₂)₃−P(O)(CH₃)₂ | 126–127 |
| 43 | 4-methylcyclohexyl | 152–153 |
| 44 | 2-methylcyclohexyl | 112–114 |
| 45 | 2,6-dimethylphenyl | 55–56 |
| 46 | phenyl | 196–197 |
| 47 | −(CH₂)₂−C₆H₄−Cl | 158–159 |
| 48 | −CH(CH₃)−(CH₂)₂−COOCH₃ | 77–79 |
| 49 | −(CH₂)₃−N(CH₃)₂ | non-distillable oil |
| 50 | −(CH₂)₂−N(CH₃)₂ | 110–114 |
| 51 | −CH(C₂H₅)−CH₂−N(CH₃)₂ | non-distillable oil |
| 52 | −CH₂−(furyl) | 154 |
| 53 | 4-tert-butylcyclohexyl | 132–134 |
| 54 | −C₁₈H₃₅ (oleyl) | 46–48 |
| 55 | −C₁₆H₃₃ | 88–89 |
| 56 | 4-methylphenyl (tolyl) | 210 (decomp.) |
| 57 | −C₁₈H₃₇ (stearyl) | 89–90 |
| 58 | naphthyl | 70–73 |
| 59 | −C₁₁H₂₃ | 92 |
| 60 | −CH₂−C₆H₄−Cl | 140–142 |
| 61 | −CH₂−CH₂−C₆H₃(OCH₃)₂ | 142–143 |
| 62 | −C₁₀H₂₁ | 85 |
| 63 | −CH₂−C₆H₄−OCH₃ | 146–148 |
| 64 | −CH₂−CH₂−CH(CH₃)₂ | 114–115 |
| 65 | −C₁₅H₃₁ mixture with −C₁₃H₂₇ | 60–62 |
| 66 | 2-methylphenyl | 158 |
| 67 | 4-hydroxycyclohexyl | 179 (decomp.) |
| 68 | −CH₂−CH₂−C₆H₅ | 147 |
| 69 | −CH₂−CH₂−cyclohexyl | 137 |
| 70 | 4-methylphenyl | 204–205 |
| 71 | −C₁₃H₂₇ | 88 |
| 72 | 4-hydroxyphenyl | 245 (decomp.) |
| 73 | −CH₂−CH(C₂H₅)−C₄H₉ | 84–87 |
| 74 | −C₁₀H₂₁ (iso) | non-distillable oil |
| 75 | −(CH₂)₃−O−CH(CH₃)₂ | 60 |

Table-continued

| Example | R | Melting point °C |
|---|---|---|
| 76 | 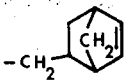 -CH₂- | 190 |
| 77 | —(CH₂)₃—O—CH₂—CH—C₄H₉<br>　　　　　　　　　　│<br>　　　　　　　　　　C₂H₅ | 70–73 |
| 78 | 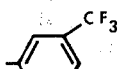 | 310–311 |
| 79 | —CH—CH₂—CH—CH₃<br>　│　　　　│<br>　CH₃　　CH₃ | 73 |
| 80 | —C₇H₁₃ mixture with C₉H₁₇ | non-distill-able oil |
| 81 | —C₁₂H₂₅ mixture with C₁₈H₃₇ | 76–77 |
| 82 |  | 71–74 |
| 83 | -CH₂- 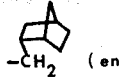 (endo) | 210–212 |
| 84 | -CH₂- 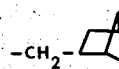 (exo) | 178–179 |
| 85 | —(CH₂)₃O—(CH₂)₇—CH₃ (mixture with 9) | non-distill-able oil |
| 86 | —C₁₄H₂₉ | 89–90 |
| 87 | —(CH₂)₃—O—C₁₂H₂₅ (iso) | non-distill-able oil |
| 88 | 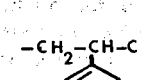 | 85–93 |
| 89 | -CH₂-CH  | 95–105 |
| 90 | -CH₂-CH₂-C -Cl)₃ | 180–182 |
| 91 | -CH₂- CH₂- CH 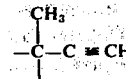 | 102–105 (decomp.) |
| 92 | 　　CH₃<br>　　│<br>—C—C≡CH<br>　　│<br>　　CH₃ | 186–187 |

Table-continued

| Example | R | Melting point °C |
|---|---|---|
| 93 | 　　C₂H₅<br>　　│<br>—C—C≡CH<br>　　│<br>　　C₂H₅ | 130–132 (decomp.) |
| 94 | 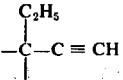 | 160–162 (decomp.) |
| 95 | 　　CH₃<br>　　│<br>—C—CH₂—CH₃<br>　　│<br>　　CH₃ | 143–144 |

B) EXAMPLES OF APPLICATION

EXAMPLE I

Cucumber plants were grown in pots, and in the 2-leaf stage treated, until drip-off, with aqueous suspensions of the compounds of Examples 1, 2 and 4 to 15. Before the treatment, newly grown leaves of the plants and the soil were carefully covered with plastic sheets in such a manner that they were not touched by the spray liquor.

The application concentrations were 2000, 1000, 500, 250 and 125 mg of active substance per liter of spray liquor. As comparative agent, benomyl (1-N-butyl-carbamoyl-2-methoxycarbonylamino-benzimidazole) was used.

After drying of the sprayed layer, the protective sheets were removed and the plants placed in a greenhouse. When the 4th and 5th leaves had developed, the plants were heavily infested with conidia of cucumber mildew (Erysiphe cichoracearum) and subsequently placed in a moisture chamber at a temperature of 22°C and a relative atmospheric humidity of 100 %. After a residence time of 24 hours, the plants were transferred to a greenhouse having a high relative atmospheric humidity (80 to 90 %) and a temperature of from 22° to 23°C, where they were kept until the outbreak of the disease.

The evaluation of the infection was carried out visibly, as usual, and the infection degree is expressed in % of infested leaf area as compared to untreated, infested control plants. The results are shown in Table I.

EXAMPLE II

Garden earth was mixed in a shaking machine for 10 minutes with the compounds of the invention cited in Example I in application amounts of 10, 5, 2.5, 1.25, 0.6 and 0.3 mg of active substance/kg of earth. As comparative agent, benomyl was used in the same application amounts as the preparations of the invention.

Pots were charged with the earth so treated and 10 grains each of winter wheat of the of the brand Heine VII were sown, before the pots were placed in a greenhouse having a high atmospheric humidity and a temperature of 22°C for germination. After emergence of the wheat, the plants, in the 4- to 5-leaf stage, were heavily infested with conidia of the powdery mildew of cereals (Erysiphe graminis). After an incubation period of 14 days, the plants were visibly examined for infection with mildew. The degree of infection was expressed in % of infested leaf area as compared to untreated, infested control plants. The results are indicated in Table II.

EXAMPLE III

Sugar beet plants in the 6-leaf stage were heavily infested with conidia of the beet leaf spot organism (Cercospora beticola) and placed dripping wet in a moisture chamber at 25°C and a 100 % relative atmospheric humidity, where they were kept for 24 hours. Subsequently, they were placed in a greenhouse having a relative atmospheric humidity of from 85 to 90 % and a temperature of from 24° to 25°C. After an infection time of 7 days, the plants were sprayed, until drip-off, with aqueous suspensions of the compounds cited in Example I.

The application concentrations were 60, 30, 15 and 7.5 mg/l of spray liquor. As comparative agent, benomyl was used in the same application concentrations.

After drying of the spray liquor, the plants were placed again in the greenhouse. After an incubation period of 3 weeks, the plants were examined for infection with beet leaf spot. The evaluation was carried out visibly, and the degree of infection expressed in % of infested leaf area, as compared to untreated, infested control plants. The results are shown in Table III.

EXAMPLE IV

Tomato plants, in the stage of completely grown 3 leaves, were heavily infested with conidia of the leaf mould of tomatoes (Cladosporium fulvum), and placed dripping wet for one day in a moisture chamber having a temperature of 25°C and a relative atmospheric humidity of 100 %. They were then transferred to a greenhouse having a relative atmospheric humidity of from 85 to 90 % and a temperature of from 23° to 25°C. After 7 days, the plants were treated with aqueous suspensions of the compounds according to Examples 16 to 24 in concentrations of 60, 30, 15 and 7.5 mg/l of spray liquor. As comparative agent, benomyl was used.

After drying of the sprayed layer, the plants were again placed in the green house and, after an incubation period of 21 days, examined for infection with leaf mould. The infection was examined visibly, as usual, and the degree of infection was expressed in % of infested leaf area relative to untreated, infested control plants.

The results are shown in Table IV.

EXAMPLE V

Wheat plants were grown in pots and in the 2-leaf stage treated, until drip-off, with the compounds cited in Example IV. The application concentrations were 2000, 1000, 500, 250 and 125 mg/l of spray liquor. As comparative agent, benomyl was used in the same concentrations of active substance as cited.

After drying of the layer of spray liquor, the plants were placed in a greenhouse, where they were kept until the 4th and 5th leaves were fully developed. In this stage, the plants were heavily infested with conidia of the powdery mildew of cereals (Erysiphe graminis), the temperature of the greenhouse was adjusted to 22° to 23°C, and the relative atmospheric humidity to 80 to 90 %, in order to create optimum infection conditions for the mildew.

After incubation period of 10 days, the plants were visibly examined for infection, and the degree of infection was expressed in % of infested area, relative to untreated, infested control plants. The results are indicated in Table V.

Example VI

Winter wheat of the Heine VII brand was homogeneously seed-treated for 10 minutes in a shaking machine with the compounds cited in Example IV and benomyl, in application amounts of 200, 100, 50 and 25 g of active substance per 100 kg of seeds.

Subsequently, 5 times 10 grains each of the treated seeds were sown in pots filled with earth, and placed in a greenhouse for germination.

When the 4th and 5th leaves of the plants had developed, the plants were heavily infested with conidia of the powdery mildew of cereals (Erysiphe graminis) and the greenhouse adjusted to a relative atmospheric humidity of from 80 to 90 % and a temperature of from 22° to 23°C.

After an incubation period of 10 days, the plants were examined for infection with mildew, and the degree of infection was expressed in % of infested leaf area, relative to untreated, infested control plants. The results are shown in Table VI.

EXAMPLE VII

Wheat plants of the Heine VII brand, in the 3-leaf stage, were infested with conidia of the powdery mildew of cereals (Erysiphe graminis) and, 3 days after the infection, treated with aqueous suspensions of the compounds according to Examples 3 and 25 to 32, until they were dripping wet. The application concentrations were 120, 60, 30 and 15 mg of active substance/l of spray liquor. As comparative agent, benomyl was used in the same application concentrations.

After drying of the sprayed layer the plants were placed in a greenhouse having a relative atmospheric humidity of from 80 to 90 % and a temperature of from 22° to 23°C.

10 Days after the treatment, the plants were visibly examined for infection with mildew. The degree of infection was expressed in % of infested leaf area, relative to untreated, infested control plants. The results of the test are indicated in Table VII.

EXAMPLE VIII

Cucumber plants in the 2-leaf stage were treated, until drip-off, with aqueous suspensions of the compounds cited in Example VII, in application concentrations of 2000, 1000, 500 and 250 mg of active substance/l of spray liquor; newly grown leaves and the soil being carefully protected by plastics sheets in such a manner that they were not touched by the spray liquor. The comparative agent was again benomyl.

After drying of the sprayed layer, the plants were placed in a greenhouse and were kept there until they had developed the 4th leaf. In this stage, all plants, including untreated control plants, were heavily infested with conidia of the cucumber mildew (Erysiphe cichoracearum), and placed in a moisture chamber having a temperature of 22°C and a relative atmospheric humidity of 100 %. After 24 hours, the plants were transferred to a greenhouse having a high relative atmospheric humidity and a temperature of from 22° to 23°C. After an incubation period of 10 days, the plants were examined visibly for infection with cucumber mildew. The degree of infection was expressed in % of infested leaf area, relative to untreated, infested control plants. The results are shown in Table VIII.

EXAMPLE IX

Rice plants in the 4-leaf stage were heavily infested with Piricularia oryzae and subsequently placed in a moisture chamber having a temperature of 25°C and a relative atmospheric humidity of 100 %. After a residence time of 24 hours, the plants were transferred to a greenhouse having a relative atmospheric humidity of 85 to 90 % and a temperature of 25° to 26°C. 4 Days after the infection, the plants were treated with the compounds cited in Example VII in application concentrations of 60, 30, 15 and 7.5 mg of active substance/1 of spray liquor. As comparative agent, benomyl was used in the same application concentrations as above.

After drying of the sprayed layer, the plants were again placed in the greenhouse and, after in incubation period of 14 days, visibly examined for infection with Piricularia oryzae. The degree of infection was expressed in % of infested leaf area, as compared to untreated, infested control plants. The results are shown in Table IX.

EXAMPLE X

Young vine plants of the Peronospora predisposed MullerThurgau brand, in the 4-leaf stage, were treated, until dripoff, with aqueous suspensions of the compounds of Examples 1 and 12 to 15. The application concentrations were 500, 250, 125 and 60 mg of active substance per liter of spray liquor. As comparative agents, benomyl (Comparative Agent I) and folpet (N-(trichloromethylthio)-phthalimide = Comparative Agent II) were used in the same concentrations of active substance as cited above.

After drying of the sprayed layer, the plants were heavily infested with a zoo-sporangia suspension of Peronospora viticola and placed dripping wet in a moisture chamber at a temperature of 20°C and a relative atmospheric humidity of 100 %. After 24 hours, the infested plants were transferred to a greenhouse having a temperature of 23°C and an atmospheric humidity of from 80 to 90 %. After an incubation period of 7 days, the plants, which had been wetted, were again placed in the moisture chamber overnight and thus the infection caused to appear. The evaluation of the infection was carried out visibly, and the degree of infection was expressed in % of infested leaf area, as compared to untreated, infested control plants. The results are listed in Table X.

EXAMPLE XI

Vine plants grown from cuttings of the Muller-Thurgau brand, were sprayed in the 4-leaf stage, until dripoff, with aqueous suspensions of the compounds cited in Example X. The application concentrations were 20, 10, 5 and 2.5 mg of active substance/1 of spray liquor. As comparative agents, benomyl and folpet were used in the same concentrations of active substance as indicated above.

After drying of the sprayed layer, the plants were placed in a greenhouse having a relative atmospheric humidity of 85 to 90 % and a temperature of 23° to 25°C, and heavily infested with conidia of the powdery mildew of vine (Oidium tuckeri).

After an incubation period of 14 days, the plants were examined for infection with Oidium, and the degree of infection was expressed in % of infested leaf area, as compared to untreated, infested control plants. The results are indicated in Table XI.

EXAMPLE XII

Tomato plants of the brand called Rheinlands Ruhm were sprayed in the 3-leaf stage with aqueous suspensions of the compounds indicated in Example X until drip-off. The application concentrations were 500, 250, 120, and 60 mg of active substance/1 of spray liquor. As comparative agents, benomyl (Comparative Agent I) and zineb (zinc-ethylene-bis-dithio-carbamate = Comparative Agent II) were used.

After drying of the sprayed layer, the plants were heavily infested with a zoo-sporangia suspension of Phytophthora infestans and placed dripping wet for 1 day in a moisture chamber having a temperature of 15°C and a relative atmospheric humidity of 100 %. Subsequently, they were transferred to a greenhouse having a temperature of 15°C and a relative atmospheric humidity of 85 to 95 %.

After an incubation time of 7 days, the plants were examined visibly for infection with Phytophthora, and the degree of infection was expressed in % of infested leaf area, as compared to untreated, infested control plants. The results are indicated in Table XII.

EXAMPLE XIII

Barley plants in the 3-leaf stage were treated, until drip-off, with aqueous suspensions of the compounds of Examples 1a, 49, 50 and 51 in application concentrations of 60 and 30 mg of active substance per liter of spray liquor. As comparative agent, the commerical product benomyl was used.

After drying of the sprayed layer, the plants were infested with conidia of Piricularia oryzae, and placed dripping wet in a moisture chamber at 25°C and a relative atmospheric humidity of 100 %. The plants were kept there for 1 day and then transferred to a greenhouse having a temperature of 25° to 26°C and a relative atmospheric humidity of 100 %.

After an incubation period of 7 days, the plants were visibly examined for infection with Piricularia, and the degree of infection was expressed in % of infested leaf area, relative to untreated, infested control plants. The results are shown in Table XIII.

EXAMPLE XIV

Celery plants in the 6-leaf stage were heavily infested with germs of the celery leaf spot (Septoria apii), and subsequently placed in a moisture chamber having a temperature of 25°C and an atmospheric humidity of 100 %. The plants were kept there for 1 day and were then transferred to a greenhouse having a temperature of 25° to 26°C and a relative humidity of 85 to 90 %.

After an incubation time of 5 days, the plants were treated, until drip-off, with aqueous suspensions of the compounds indicated in Examples 1a, 49, 50 and 51 and the comparative agent benomyl in application concentrations of 125 and 60 mg of active substance per liter of spray liquor. After drying of the spray liquor, the plants were placed again in the greenhouse and, after an incubation period of 21 days, visibly examined for infection with the celery leaf spot. The degree of infection was expressed in % of infested leaf area, relative to untreated, infested control plants (Table XIII).

EXAMPLE XV

Dwarf bush bean seeds of the brand called Andreas were well mixed for 10 minutes in a shaking machine with the compounds of Examples 1a, 49, 50 and 51 and the comparative agent benomyl, in application amounts of 100 and 50 g of active substance per 100 kg of seeds, and, the following day, sown in earth which before had been infested with a very virulent culture of Rhizoctonia solani. Four times 100 beans each were sown in pots filled with this earth.

Three weeks after emergence of the bean plants, the number of emerged plants was counted and the plants were examined for infection with Rhizoctonia. The results of this test are indicated in Table XIII.

Table I

| compound according to Example | % of leaf area infested with cucumber mildew at mg of active substance/liter of spray liquor | | | | |
|---|---|---|---|---|---|
| | 2000 | 1000 | 500 | 250 | 125 |
| 4 | 0 | 0 | 5 | 10 | 15 |
| 5 | 0 | 0 | 3 | 12 | 18 |
| 6 | 0 | 0 | 5 | 10 | 16 |
| 7 | 0 | 0 | 5 | 12 | 18 |
| 8 | 0 | 0 | 5 | 10 | 15 |
| 9 | 0 | 0 | 3 | 10 | 18 |
| 10 | 0 | 0 | 5 | 12 | 15 |
| 2 | 0 | 0 | 5 | 10 | 15 |
| 11 | 0 | 0 | 3 | 8 | 12 |
| 12 | 0 | 0 | 0 | 5 | 10 |
| 13 | 0 | 0 | 0 | 5 | 10 |
| 1 | 0 | 0 | 0 | 5 | 10 |
| 14 | 0 | 0 | 5 | 10 | 12 |
| 15 | 0 | 0 | 3 | 5 | 10 |
| benomyl | 0 | 5 | 8 | 15 | 20 |
| control plants (untreated) | 100 | 100 | 100 | 100 | 100 |

Table II

| compound acc. to Example | % of leaf area infested with powdery mildew of cereals at mg of active substanc/kg of earth | | | | | |
|---|---|---|---|---|---|---|
| | 10 | 5 | 2.5 | 1.25 | 0.6 | 0.3 |
| 4 | 0 | 0 | 0 | 5 | 12 | 25 |
| 5 | 0 | 0 | 0 | 5 | 15 | 20 |
| 6 | 0 | 0 | 0 | 5 | 12 | 20 |
| 7 | 0 | 0 | 0 | 5 | 10 | 20 |
| 8 | 0 | 0 | 0 | 5 | 10 | 25 |
| 9 | 0 | 0 | 0 | 5 | 12 | 20 |
| 2 | 0 | 0 | 0 | 5 | 10 | 20 |
| 10 | 0 | 0 | 0 | 5 | 12 | 18 |
| 11 | 0 | 0 | 0 | 5 | 10 | 15 |
| 12 | 0 | 0 | 0 | 0 | 5 | 12 |
| 13 | 0 | 0 | 0 | 0 | 5 | 10 |
| 1 | 0 | 0 | 0 | 0 | 3 | 10 |
| 14 | 0 | 0 | 0 | 3 | 5 | 12 |
| 15 | 0 | 0 | 0 | 5 | 8 | 15 |
| benomyl | 0 | 3 | 5 | 10 | 20 | 35 |
| control plants (untreated) | 100 | 100 | 100 | 100 | 100 | 100 |

Table III

| compound according to Example | % of leaf area infested with Cercospora at mg of active substance/liter spray liquor | | | |
|---|---|---|---|---|
| | 60 | 30 | 15 | 7.5 |
| 4 | 0 | 0 | 8 | 15 |
| 5 | 0 | 0 | 8 | 15 |
| 6 | 0 | 0 | 5 | 10 |
| 7 | 0 | 0 | 5 | 10 |
| 8 | 0 | 0 | 5 | 12 |
| 9 | 0 | 0 | 8 | 15 |
| 2 | 0 | 0 | 5 | 10 |
| 10 | 0 | 0 | 5 | 12 |
| 11 | 0 | 0 | 8 | 12 |
| 12 | 0 | 0 | 5 | 10 |
| 13 | 0 | 0 | 3 | 8 |
| 1 | 0 | 0 | 0 | 5 |
| 14 | 0 | 0 | 5 | 10 |
| 15 | 0 | 0 | 8 | 15 |
| benomyl | 0 | 3 | 15 | 20 |

Table III-continued

| compound according to Example | % of leaf area infested with Cercospora at mg of active substance/liter spray liquor | | | |
|---|---|---|---|---|
| | 60 | 30 | 15 | 7.5 |
| control plants (untreated) | 100 | 100 | 100 | 100 |

Table IV

| compound acc. to Example | % of leaf area infested with Cladosporium at mg of active substance/liter of spray liquor | | | |
|---|---|---|---|---|
| | 60 | 30 | 15 | 7.5 |
| 16 | 0 | 0 | 5 | 10 |
| 17 | 0 | 0 | 5 | 10 |
| 18 | 0 | 0 | 3 | 12 |
| 19 | 0 | 0 | 5 | 10 |
| 20 | 0 | 0 | 8 | 15 |
| 21 | 0 | 0 | 5 | 10 |
| 22 | 0 | 0 | 8 | 15 |
| 23 | 0 | 0 | 5 | 12 |
| 24 | 0 | 0 | 8 | 15 |
| benomyl | 5 | 12 | 20 | 28 |
| control plants (untreated) | 100 | 100 | 100 | 100 |

Table V

| compound acc. to Example | % of infection with powdery mildew of cereals at mg of active substance/liter of spray liquor | | | | |
|---|---|---|---|---|---|
| | 2000 | 1000 | 500 | 250 | 125 |
| 16 | 0 | 0 | 5 | 10 | 18 |
| 17 | 0 | 0 | 3 | 8 | 15 |
| 18 | 0 | 0 | 0 | 10 | 15 |
| 19 | 0 | 0 | 0 | 5 | 12 |
| 20 | 0 | 0 | 0 | 8 | 15 |
| 21 | 0 | 0 | 0 | 5 | 10 |
| 22 | 0 | 0 | 0 | 5 | 12 |
| 23 | 0 | 0 | 0 | 3 | 10 |
| 24 | 0 | 0 | 0 | 5 | 15 |
| benomyl | 0 | 3 | 8 | 15 | 28 |
| control plants (untreated) | 100 | 100 | 100 | 100 | 100 |

Table VI

| compound acc. to Example | % of mildew infection after seeds treatment with g of active substance/100 kg of seeds | | | |
|---|---|---|---|---|
| | 200 | 100 | 50 | 25 |
| 16 | 0 | 0 | 5 | 12 |
| 17 | 0 | 0 | 5 | 10 |
| 18 | 0 | 0 | 3 | 10 |
| 19 | 0 | 0 | 0 | 5 |
| 20 | 0 | 0 | 5 | 10 |
| 21 | 0 | 0 | 0 | 5 |
| 22 | 0 | 0 | 3 | 8 |
| 23 | 0 | 0 | 0 | 5 |
| 24 | 0 | 0 | 3 | 10 |
| benomyl | 0 | 5 | 10 | 18 |
| control plants (untreated) | 100 | 100 | 100 | 100 |

Table VII

| compound acc. to Example | % of infestation with powdery mildew of cereals at mg of active substance/liter of spray liquor | | | |
|---|---|---|---|---|
| | 120 | 60 | 30 | 15 |
| 25 | 0 | 0 | 5 | 8 |
| 26 | 0 | 0 | 5 | 10 |
| 3 | 0 | 0 | 3 | 8 |
| 27 | 0 | 0 | 5 | 10 |
| 28 | 0 | 0 | 5 | 8 |
| 29 | 0 | 0 | 8 | 10 |
| 30 | 0 | 0 | 5 | 10 |
| 31 | 0 | 0 | 5 | 8 |
| 32 | 0 | 0 | 3 | 5 |
| benomyl control plants | 0 | 5 | 8 | 15 |

Table VII-continued

| compound acc. to Example | % of infestation with powdery mildew of cereals at mg of active substance/liter of spray liquor | | | |
|---|---|---|---|---|
| | 120 | 60 | 30 | 15 |
| (untreated) | 100 | 100 | 100 | 100 |

Table VIII

| compound acc. to Example | % of cucumber mildew infection at mg of active substance/liter of spray liquor | | | |
|---|---|---|---|---|
| | 2000 | 1000 | 500 | 250 |
| 25 | 0 | 0 | 5 | 15 |
| 26 | 0 | 0 | 8 | 15 |
| 3 | 0 | 0 | 3 | 10 |
| 27 | 0 | 0 | 5 | 10 |
| 28 | 0 | 0 | 5 | 10 |
| 29 | 0 | 0 | 8 | 15 |
| 30 | 0 | 0 | 3 | 10 |
| 31 | 0 | 0 | 3 | 10 |
| 32 | 0 | 0 | 5 | 12 |
| benomyl | 3 | 10 | 15 | 28 |
| control plants (untreated) | 100 | 100 | 100 | 100 |

Table IX

| compound acc. to Example | % of piricularia infection at mg of active substance/liter of spray liquor | | | |
|---|---|---|---|---|
| | 60 | 30 | 15 | 7.5 |
| 25 | 0 | 0 | 3 | 10 |
| 26 | 0 | 0 | 5 | 12 |
| 3 | 0 | 0 | 3 | 10 |
| 27 | 0 | 0 | 5 | 15 |
| 28 | 0 | 0 | 3 | 12 |
| 29 | 0 | 0 | 8 | 18 |
| 30 | 0 | 0 | 5 | 18 |
| 31 | 0 | 0 | 0 | 5 |
| 32 | 0 | 0 | 3 | 10 |
| benomyl | 0 | 5 | 18 | 25 |
| control plants (untreated) | 100 | 100 | 100 | 100 |

Table X

| compound acc. to Example | % of Peronospora infection at mg of active substance/liter of spray liquor | | | |
|---|---|---|---|---|
| | 500 | 250 | 125 | 60 |
| 15 | 0 | 3 | 5 | 10 |
| 12 | 0 | 0 | 5 | 8 |
| 13 | 0 | 0 | 3 | 5 |
| 1 | 0 | 0 | 0 | 3 |
| 14 | 0 | 0 | 3 | 8 |
| CA I | 100 | 100 | 100 | 100 |
| CA II | 0 | 3 | 5 | 10 |
| control plants (untreated) | 100 | 100 | 100 | 100 |

Table XI

| compound acc. to Example | % of Oidium infection of the vine at mg of active substance/liter of spray liquor | | | |
|---|---|---|---|---|
| | 20 | 10 | 5 | 2.5 |
| 15 | 0 | 0 | 8 | 15 |
| 12 | 0 | 0 | 5 | 15 |
| 13 | 0 | 0 | 0 | 8 |
| 1 | 0 | 0 | 0 | 8 |
| 14 | 0 | 0 | 5 | 12 |
| CA I | 0 | 8 | 15 | 23 |
| CA II | 65 | 80 | 100 | 100 |
| control plants (untreated) | 100 | 100 | 100 | 100 |

Table XII

| compound acc. to Example | % of Phytophthora infection at mg of active substance/liter of spray liquor | | | |
|---|---|---|---|---|
| | 500 | 250 | 120 | 60 |
| 15 | 0 | 0 | 5 | 13 |
| 12 | 0 | 0 | 5 | 10 |
| 13 | 0 | 0 | 5 | 8 |
| 1 | 0 | 0 | 3 | 5 |
| 14 | 0 | 3 | 5 | 10 |
| CA I | 100 | 100 | 100 | 100 |
| CA II | 0 | 3 | 5 | 12 |
| control plants (untreated) | 100 | 100 | 100 | 100 |

Table XIII

| compound acc. to Example | % of infested leaf area with Piricularia at mg of active subst/1. | | with Septoria of spray liquor | | % of Rhizoctonia infested plants at g of active substance/ 100 kg of seeds | |
|---|---|---|---|---|---|---|
| | 60 | 30 | 125 | 60 | 100 | 50 |
| 1a | 0 | 8 | 0 | 8 | 0 | 8 |
| 49 | 0 | 5 | 0 | 3 | 0 | 8 |
| 50 | 0 | 5 | 0 | 5 | 0 | 5 |
| 51 | 0 | 12 | 0 | 8 | 0 | 10 |
| comp. agent benomyl | 0 | 10 | 0 | 5 | 0 | 10 |
| untreated infested plants | 100 | 100 | 100 | 100 | 100 | 100 |

What is claimed is:

1. A fungicidal composition which comprises an effective amount of a triazino-benzimidazole of the formula

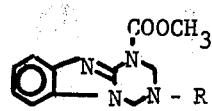

in which R is alkyl having from 1 to 18 carbon atoms; alkenyl having from 3 to 18 carbon atoms, alkinyl having from 2 to 8 carbon atoms, cycloalkyl having from 3 to 12 carbon atoms, optionally substituted by one or more alkyl groups having from 1 to 4 carbon atoms or by hydroxy; cyclohexylalkyl, cyclohexylalkenyl, or cyclohexylalkinyl each having from 1 to 3 carbon atoms in the chain, endomethylene-cyclohexylmethyl, endomethylene-cyclohexenylmethyl, tricyclodecyl, or tricyclodecenyl; phenalkyl, diphenylalkyl or triphenylalkyl each having from 1 to 6 carbon atoms in the alkylene radical, the phenyl nuclei of which being optionally substituted by halogen, alkyl, alkoxy or alkylthio, each having from 1 to 4 carbon atoms or by di-$(C_1$-$C_4)$-alkylamino; phenyl or naphthyl, optionally being substituted by alkyl of from 1 to 4 carbon atoms, halogen, halogenoalkyl of from 1 to 4 carbon atoms, trifluoromethyl, hydroxy, alkoxy of from 1 to 4 carbon atoms, phenoxy or (C₁-C₄)-alkylthio; di-(C₁-C₄)-alkylamino-(C₂-C₆)-alkyl; hydroxy-(C₂-C₁₂)-alkyl, (C₂-C₁₈)-alkoxyalkyl or dialkoxyalkyl, (C₂-C₁₈)-alkylmercaptoalkyl, (C₃-C₉)-dialkylphosphinyl-alkyl, furfuryl, morpholino-(C₁-C₄)-alkyl, pyrrolidino-(C₁-C₄)-alkyl, piperidino-(C₁-C₄)-alkyl or (C₂-C₁₂)-carbalkoxylalkyl in admixture with an inert carrier, and a dispersing agent.

2. A fungicidal composition as defined in claim 1 in which the benzimidazole compound is one in which R is

3. A fungicidal composition as defined in claim 1 in which the benzimidazole compound is one in which R is

4. A method for combating fungal diseases in plants which comprises applying to the locus to be protected or already infected an effective amount of the fungicidal composition as claimed in claim 1.

5. The method defined in claim 4 in which the benzimidazole compound has the formula

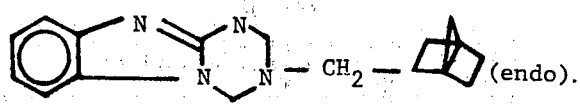

6. The method defined in claim 4 in which the benzimidazole compound has the formula

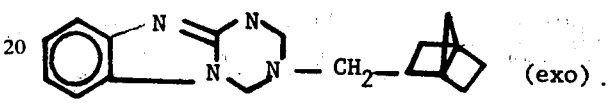

* * * * *